United States Patent [19]

Uhrin

[11] Patent Number: 4,970,165

[45] Date of Patent: Nov. 13, 1990

[54] CELL HARVESTER TRAY

[75] Inventor: Michael G. Uhrin, Pittsburgh, Pa.

[73] Assignee: Montefiore Hospital Association of Western Pennsylvania, Pittsburgh, Pa.

[21] Appl. No.: 402,554

[22] Filed: Sep. 5, 1989

[51] Int. Cl.[5] .................... C12M 1/00

[52] U.S. Cl. .................... 435/287; 435/301; 435/284; 422/102

[58] Field of Search .................... 435/301, 284, 297–300, 435/310, 287; 422/102, 58, 65, 101; 206/84, 197, 203, 329, 385, 419, 446, 557, 558, 560, 563, 564, 565, 524.1; 220/21; 356/244, 246, 440; 436/809

[56] References Cited

U.S. PATENT DOCUMENTS

| | | | |
|---|---|---|---|
| 3,286,583 | 11/1966 | Ferrari | 422/102 X |
| 3,375,434 | 4/1968 | Bates | 356/244 X |
| 3,390,783 | 7/1968 | Quackenbush, Jr. | 356/244 X |
| 3,544,225 | 12/1970 | Wattenburg et al. | 356/440 |
| 3,895,507 | 10/1976 | Litz et al. | 356/244 X |
| 4,254,795 | 5/1979 | Thorne | 422/102 X |
| 4,286,637 | 9/1981 | Wilson | 422/102 X |
| 4,801,428 | 1/1989 | Homolko et al. | 422/102 X |

FOREIGN PATENT DOCUMENTS

| | | | |
|---|---|---|---|
| 1116157 | 6/1968 | United Kingdom | 206/563 |

*Primary Examiner*—Larry Jones

*Attorney, Agent, or Firm*—Harry B. Keck

[57] ABSTRACT

A cell harvester tray formed from lightweight plastic for holding scintillation vials. In one embodiment the tray has a plurality of parallel, aligned wells, each well being adapted to support one scintillation vial. In an alternative embodiment the tray is provided with generally parallel aligned bores extending through a top surface and adapted to press-fit a scintillation vial whereby all of the top edges of the scintillation vials are maintained in a common level. Guide means are molded into the block for aligning the block in a cell harvester.

13 Claims, 2 Drawing Sheets

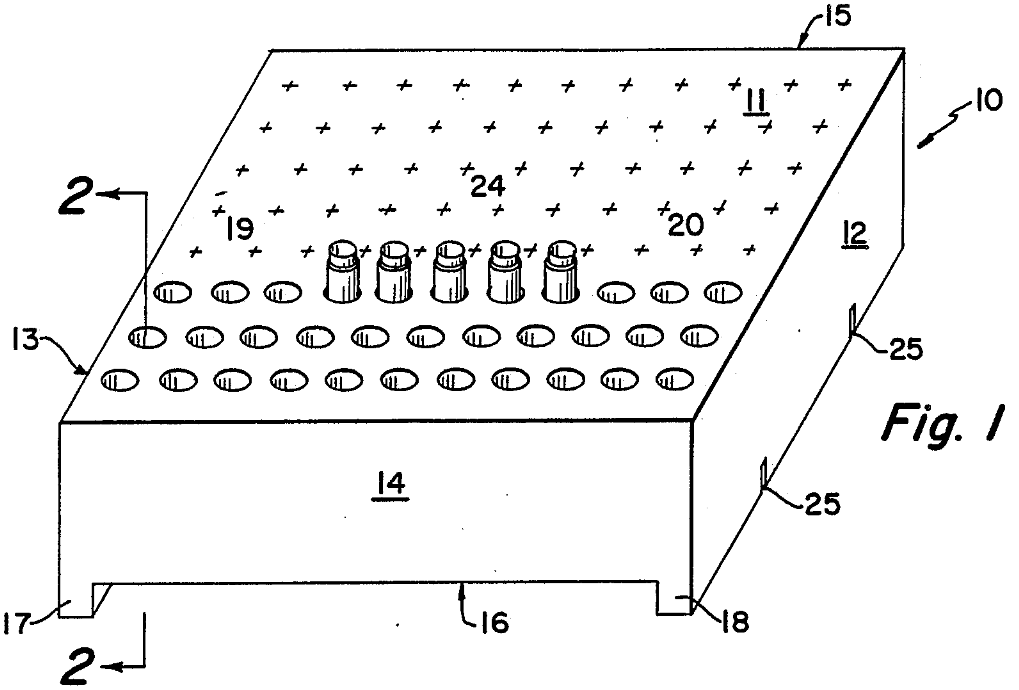
Fig. 1
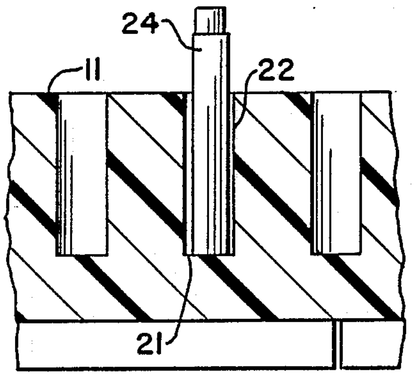
Fig. 2-A
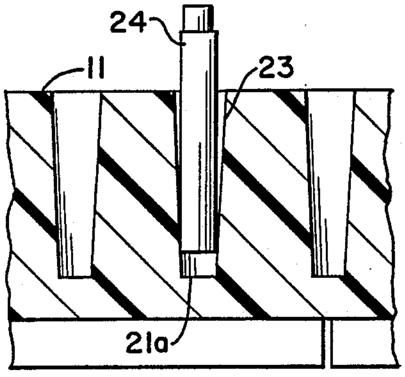
Fig. 2-B
Fig. 3
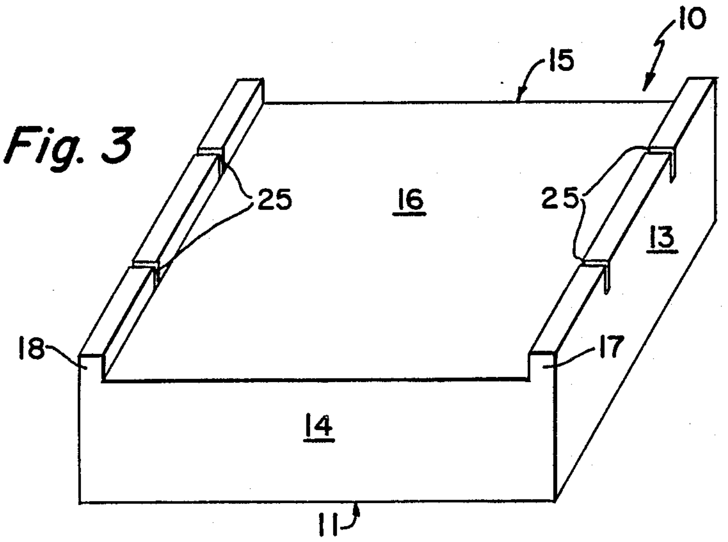
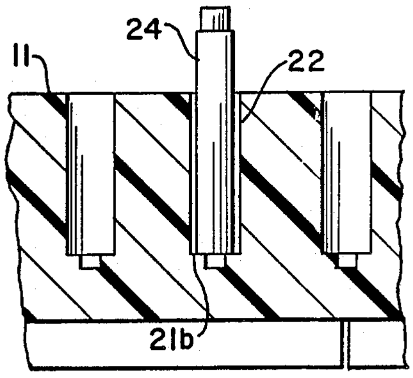
Fig. 2-C

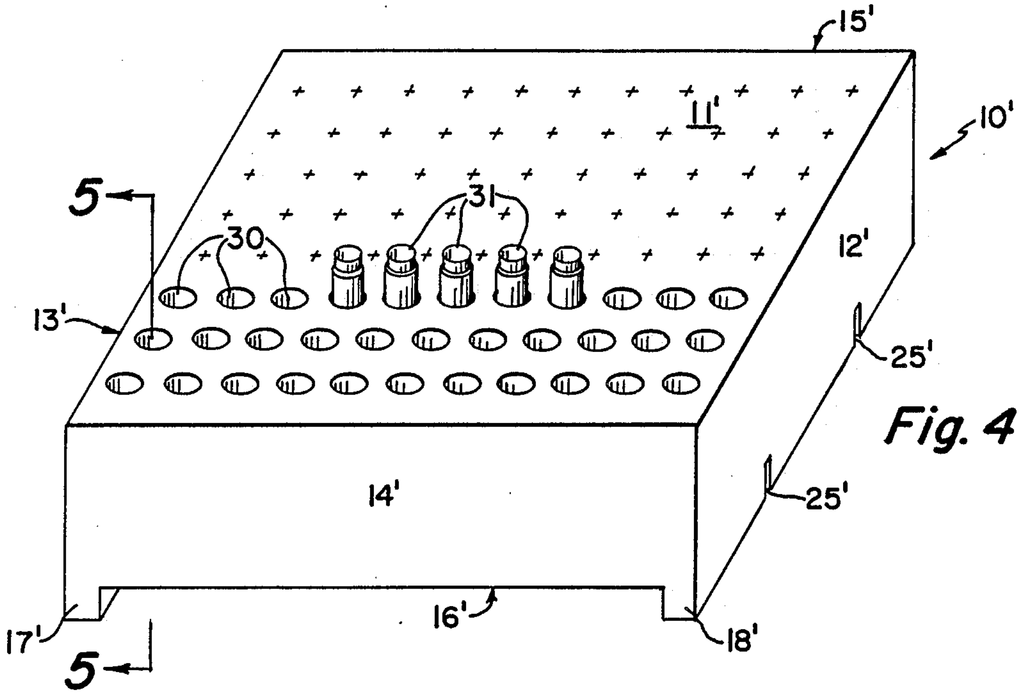
Fig. 4
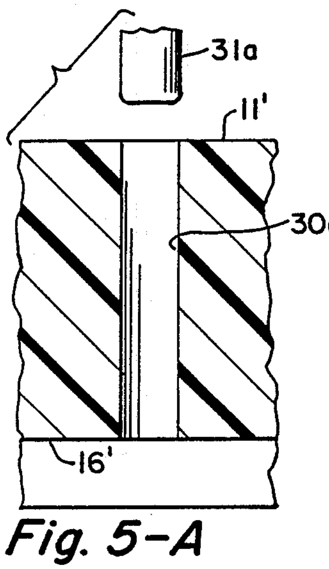
Fig. 5-A
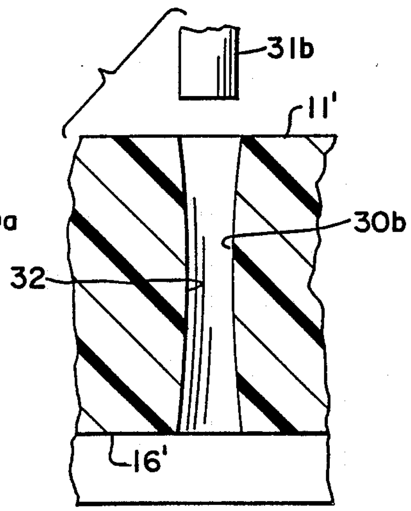
Fig. 5-B
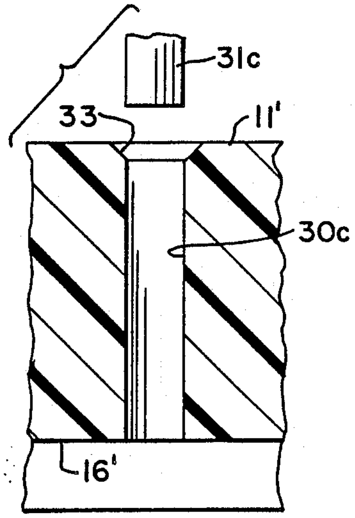
Fig. 5-C
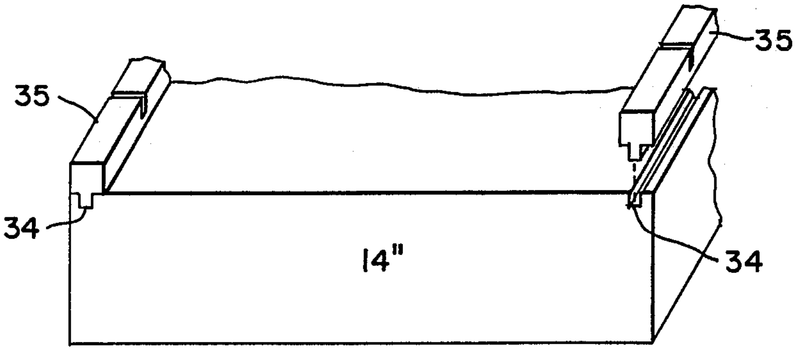
Fig. 6
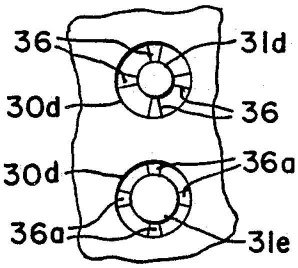
Fig. 7

CELL HARVESTER TRAY

FIELD OF THE INVENTION

The present invention relates to an improvement in a cell harvester tray of the type which is employed to contain multiple scintillation vials for transport and filling.

BACKGROUND OF THE INVENTION

Scintillation vials are employed to contain specimens which are analyzed in equipment known as scintillation counters. A scintillation counter measures radiation in a particular vial. Scintillation counting is relatively rapid and numerous analyses can be conducted in a short period of time. The preparation of samples requires multiple segregated vials (called scintillation vials) which are filled with specimens, solvents, and a filtration disc onto which cell components are deposited. Typically, scintillation vials are supported in trays having a certain alignment, for example, eight rows of twelve samples each. The trays are filled with fresh scintillation vials (sometimes glass, but normally plastic cylindrical bottles). The tray containing multiple scintillation vials is placed into a machine called a cell harvester which dispenses the filter disc, a particular reagent or solvent or specimen into a group of the vials. Repetitive advances of the tray and dispensing of the material into a next group of the vials occurs; the tray advances then again dispensing new discs into a further group of vials, etc., until all of the vials have received a pre-determined quantity of the materials. Sometimes the filled scintillation tray is introduced into a dispensing machine which deposits scintillation fluid into each of the scintillation vials in a similar step-wise multiple vial filling process.

Existing scintillation vial trays are fabricated from metal plates having multiple aligned circular openings and having a bottom shelf. The operators individually fill the multiple openings of the existing scintillation vial trays manually and introduce the filled metal trays into the described dispersing equipment for vial filling.

After the vials have been analyzed in the scintillation counter, the vials are discarded in a container for ultimate disposal as radiation hazardous materials. The scintillation vial tray which is a non-hazardous, is recovered for refilling and reuse. The existing scintillation vial trays are relatively expensive, require substantial manual effort of skilled professional operators.

STATEMENT OF THE INVENTION

According to the present invention a scintillation vial tray is provided in the form of a unitary plastic block having a rectangular top surface and containing multiple wells or bores each having an opening in the top surface and extending normally into the block away from the top surface. The individual wells or bores are generally cylindrical but may have a taper with the wide diameter adjacent to the top surface of the plastic block. The wells also may have a shelf at the bottom to provide a resting surface for the bottom end of a scintillation vial. Within these bores are splines which will permit the use of both 7 ml and 5 ml scintillation vials. If bores are provided extending through the bottom surface of the plastic block, the bores press-fit against the outer cylindrical wall of the contained vial.

The block can be equipped with guide means such as lengthwise beads or grooves to provide alignment of the tray while it is in a dispensing or filling machine. Appropriate indexing means such as slots in the alignment beads may be provided to establish the step-wise positions of the scintillation vial tray for step-wise vial leading within a dispensing or filling machine.

DESCRIPTION OF THE DRAWINGS

FIG. 1 is a respective illustration of a scintillation vial tray according to one embodiment of the invention.

FIGS. 2-A, 2-B, 2-C are sectional views taken along the line 2—2 of FIG. 1 illustrating alternative embodiments of the well construction.

FIG. 3 is a respective view of the bottom surface of the scintillation vial tray of FIG. 1.

FIG. 4 is a perspective illustration of a scintillation vial tray according to an alternative embodiment of the invention.

FIGS. 5-A, 5-B, 5-C are sectional views taken along the line 5—5 of FIGS. 4 illustrating alternative embodiments of the embodiment of FIG. 4.

FIG. 6 is a fragmentary, perspective bottom view of a scintillation vial tray showing an alternative embodiment.

FIG. 7 is a fragmentary plan view of bores showing inwardly directed splines.

DESCRIPTION OF THE PREFERRED EMBODIMENTS

The scintillation vial tray of this invention is formed by molding or otherwise shaping a generally rectangular block of lightweight plastic, preferably foamed plastic and more particularly expanded polystyrene. The lightweight plastic has a density of 1 to 5 pounds per cubic foot. In one embodiment of the invention, shown in FIGS. 1, 2, 3, the plastic block 10 has a top surface 11, side surfaces 12, 13 (not seen in FIG. 1) and surfaces 14, 15 (not seen in FIG. 1) and a bottom surface 16 (not seen in FIG. 1). Linear beads 17, 18 extend parallel to the surface 12 along the underside of the block 10. The beads 17, 18 function as an alignment means for the block 10 in a dispensing or filling machine. While two beads 17, 18 are illustrated, it is evident that one bead will satisfy the alignment/function so long as the bead is generally parallel to a side surface 12(13) of the block 14.

An array of aligned wells 19 is provided in the block 10 with open upper ends 20 in the top surface 11 and bottom ends 21 (21*a*, 21*b*) in the interior of the block 10. Each well has side walls which may be generally cylindrical side walls 22 as shown in FIG. 2-A; or may be tapered side walls 23 as shown in FIG. 2-B.

Individual scintillation vials 24 are positioned, closed end down, in the wells 19. The vial 24 may rest upon the bottom wall 21 as shown in FIG. 2-A. The bottom wall of the scintillation vial 24, as shown in FIG. 2-B, may be elevated above the bottom wall 21*a* of the well as a result of the engagement of the side wall of the vial 24 with the tapered side wall 23. The vial 24 may rest upon a shelf 21*b* as shown at the bottom of the well in FIG. 2-C.

The scintillation vial tray may be further equipped with indexing means such as slots 25 with beads 17, 18 to provide an index for positioning the block 10 within a dispensing or filling machine.

A preferred tray is fabricated from expanded polystyrene beads and has a density of about 1 to 1.5 pounds per cubic foot. Scintillation vials typically are about 14.2 mm diameter and 58 mm high. The block 10, holding 8 rows of 12 wells 19 will have a top surface about 19.3 cm by 26.1 cm, and a height of about 4.25 cm. The beads 17, 18 are about 1.25 cm wide.

BENEFITS OF THE INVENTION

The scintillation vial tray of this invention is a low cost, lightweight device which can be factory-filled with scintillation vials and which thereby avoids the need for skilled professional workers to insert vials into scintillation vial trays of the prior art. The trays are relatively low in cost and can be discarded after a single use. The scintillation vials with their radioactive contents can be collected in a container for disposal as radiation hazard substances. The plastic block 10 can be discarded with ordinary municipal waste materials. The plastic block 10, of course can be reused repeatedly.

An alternative embodiment of the present invention is illustrated in FIGS. 4, 5-A, 5-B, and 5-C. In the alternative embodiment, the thickness of the block 10' is reduced and the tray is equipped with generally cylindrical bores 30 instead of the wells 19 of the embodiment of FIGS. 1, 2-A, 2-B, 2-C and 3. The bores 30 preferably have a diameter suitable for a press-fit engagement of scintillation vials 31. The bores 30 extend entirely through the block 10', as seen in FIGS. 5-A, 5-B and 5-C. The bores 30 may have a variety of profiles. In FIG. 5-A the bore 30 has a cylindrical profile corresponding to the diameter of a scintillation vial 31*a*. If the vial 31*a* has a rounded closed end as shown, the vial can be easily inserted into the cylindrical bore 30. An alternative embodiment illustrated in FIG. 5-B has the bore 30*b* provided with a narrowed central region 32 so that the bore 30*b* has an hourglass configuration. A scintillation vial 31*b* readily fits into the bore 30*b* and is engaged lightly but firmly by the narrow central portion 32 of the bore 30*b*.

The bore 30 may be provided with a countersink enlargement 33 as illustrated in FIG. 5-C. The closed end of a scintillation of a vial 31*c* can be readily urged into alignment with the bore 30*c*.

In a further embodiment illustrated in FIG. 6, the block 14" is provided with lengthwise grooves 34 which receive lengthwise bars 35 which may be formed from metal or a hard plastic. The bars 35 constitute an alignment means for guiding the tray 14" through dispensing or filling apparatus. Grooves 36 may be provided as index means on the bars 35.

In an alternative embodiment of FIG. 7 each bore 30*d* is provided with lengthwise splines 36(36*a*) which project inwardly toward the center of the bore 30*d* and serve to engage a scintillation vial 31*d*. The splines 36 will press-fit a 5 ml diameter vial 31*d* and support the vial 31*d* with the top edges at a common level with top edges of other vials. A 7 ml diameter vial 31*e* can be supported by the splines 36*a* which readily compress when the vial 31*e* is installed. The splines 36(36*a*) may be continuous along the length of the bore 30*d* or may comprise discontinuous inward tabs.

I claim:

1. A cell harvester tray for scintillation vials having an open upper portion and a closed lower portion comprising:

a molded lightweight plastic block having a rectangular top surface, a plurality of wells in said block, each well opening at the said top surface and each well adapted to receive and support the said lower closed portion of one scintillation vial; with said open upper portions aligned in a common plane above said rectangular top surface; guide means in said block for aligning said block in a cell harvester.

2. The cell harvester tray of claim 1 wherein the said plastic block is expanded polystyrene.

3. The cell harvester tray of claim 1 wherein the said plastic block is a foamed plastic material having a density of 1 to 5 pounds per cubic foot.

4. The cell harvester tray of claim 1 wherein the said guide means are parallel beads extended from a surface of said block, parallel to an edge surface of said block.

5. The cell harvester tray of claim 4 including indexing means comprising openings in at least one of the said beads.

6. The cell harvester tray of claim 1 including indexing means in said block to serve as positioning devices.

7. The cell harvester tray of claim 1 wherein each of the said wells has a tapered side wall which is wider at the top surface and narrower at the bottom of the well.

8. The cell harvester tray for scintillation vials comprising:

A molded lightweight plastic block having a rectangular top surface, a plurality of bores in said block, each bore extending from said top surface through said block and through an opposing bottom surface; each bore being adapted to engage by press-fit the side wall of a cylindrical scintillation vial and thereby to support said open upper portions aligned in a common plane above said top surface; guide means molded in said block for aligning said block in a cell harvester.

9. The cell harvester tray of claim 8 wherein the said plastic block is expanded polystyrene.

10. The cell harvester tray of claim 8 wherein the said plastic block is a foamed plastic material having a density of 1 to five pounds per cubic foot.

11. The cell harvester tray of claim 8 wherein each said bore has multiple inwardly directed lengthwise splines comprising part of the said sidewall and adapted to engage a scintillation vial within said bore.

12. The cell harvester of claim 11 wherein the said guide means comprises at least one bead in said block along the bottom surface thereof, said bead being generally parallel to a side surface of said block.

13. A cell harvester tray for scintillation vials having an open upper portion and a closed lower portion, said tray fabricated from a lightweight plastic block having a rectangular top surface; means within said block to support multiple scintillation vials with the top edges of said scintillation vials at a common level above said top surface of said block; and at least one groove in the bottom surface of said block parallel to a side surface of said block, a metal or hard plastic bar engaged in said groove to function as a guide means for aligning said block in a cell harvester.

* * * * *